United States Patent [19]

LaViola et al.

[11] Patent Number: 4,996,992

[45] Date of Patent: Mar. 5, 1991

[54] AUTOMATIC BLOOD PRESSURE MEASUREMENT IN HYPERBARIC CHAMBER

[75] Inventors: John LaViola, Orange; William C. Watson, Greenwich, both of Conn.

[73] Assignee: CAS Medical Systems, Inc., Branford, Conn.

[21] Appl. No.: 410,130

[22] Filed: Sep. 20, 1989

[51] Int. Cl.$^5$ ............................................. A61B 5/022
[52] U.S. Cl. .................................................. 128/677
[58] Field of Search ................... 128/205.26, 677, 674, 128/672, 668, 683; 600/22

[56] References Cited

U.S. PATENT DOCUMENTS 3,485,238 12/1969 Kostrov .............................. 128/683

Primary Examiner—William E. Kamm
Assistant Examiner—Robert L. Nasser, Jr.
Attorney, Agent, or Firm—William W. Jones

[57] ABSTRACT

Blood pressure measurements are performed on subjects disposed in hyperbaric chambers. The measurements are made by an automatic blood pressure monitoring instrument having a differential pressure transducer component. The reference side of the pressure transducer is open to the pressure in the hyperbaric chamber. A rotary vane pump is used to inflate the cuff with the inflation fluid supply from within the hyperbaric chamber, and exhaust from deflating the cuff is vented back into the hyperbaric chamber.

11 Claims, 1 Drawing Sheet

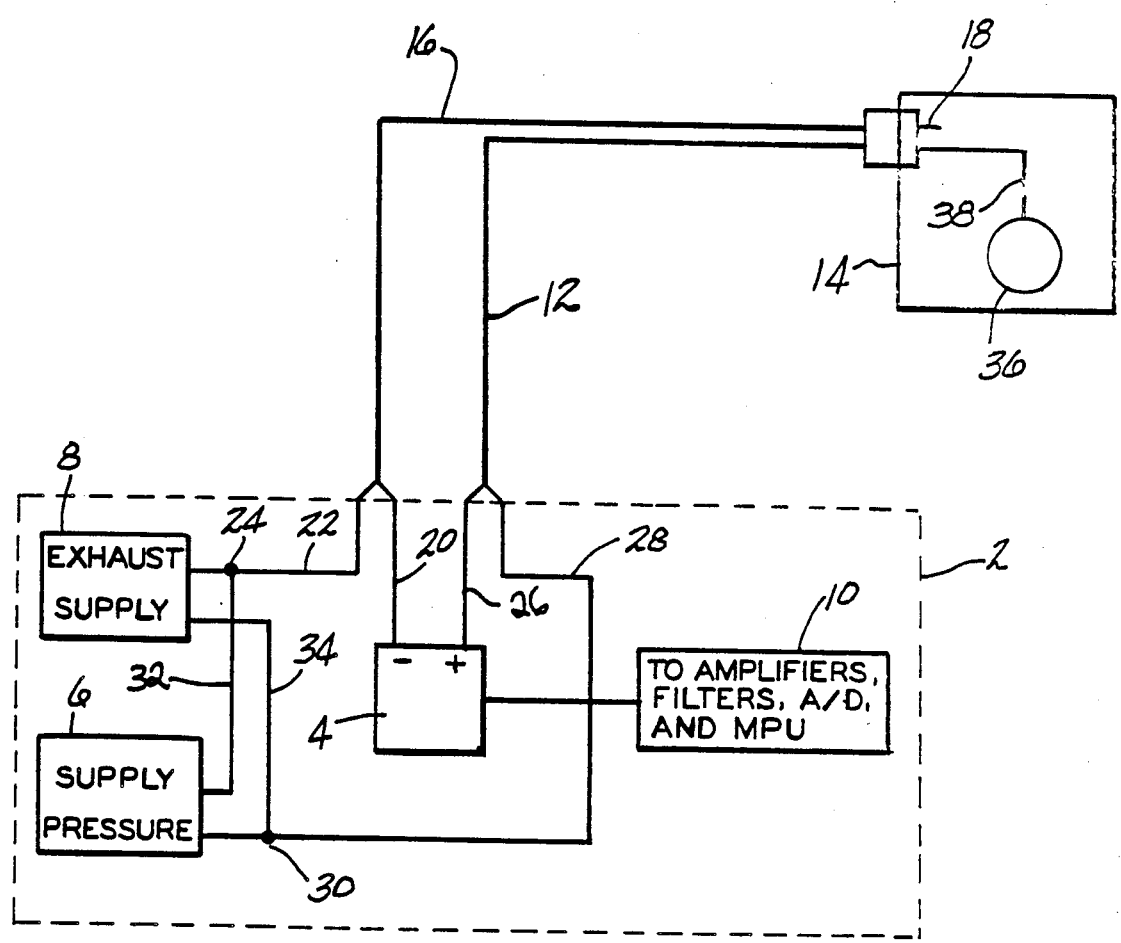

AUTOMATIC BLOOD PRESSURE MEASUREMENT IN HYPERBARIC CHAMBER

FIELD OF THE INVENTION

This invention relates to the automatic measurement of the blood pressure of a subject who is confined to a hyperbaric chamber.

DESCRIPTION OF RELATED ART

Hyperbaric chambers have been used for treating Caisson disease, or "bends" in deep sea divers, tunnel crew personnel, and the like persons exposed to high pressure environments. These chambers contain high purity oxygen at super atmospheric pressure, typically 3 ATM or greater.

Recently, it has been discovered that subjects who have undergone skin grafts will be benefitted by being placed in a hyperbaric chamber because the grafts heal faster in this high pressure pure oxygen environment. This latter use of the hyperbaric chamber requires that the subject remain in the chamber for longer periods of time than the Caisson disease treatment, and also involved subjects whose vital signs must be closely monitored.

Investigations are also ongoing relative to the use of hyperbaric chambers in the treatment of post heart attack victims. The latter treatment also requires extended periods of confinement in the hyperbaric chamber, and close monitoring of patient vital signs.

One of the vital signs which must be closely monitored is the subject's blood pressure. Most, if not all modern hospitals use automated blood pressure monitors on patients, which inflate the pressure cuff automatically periodically and measure and record the systolic, mean and diastolic blood pressure values of the patient. These devices typically include onboard microprocessors, pumps and electrically operated valves for controlling gas flow, and for taking and storing pressure values. A differential pressure transducer is included to measure cuff pressures and cuff pressure oscillations caused by arterial pulses. Up to the present time these automatic blood pressure monitors have not been suitable for use in hyperbaric chambers because of inflation problems which can only be overcome by using inordinately large pumps when the monitor is outside of the chamber because of the need to overcome chamber pressure with ambient air pumped into the cuff; and because the pure oxygen atmosphere precludes placing the monitor inside of the chamber.

SUMMARY OF THE INVENTION

This invention relates to an automatic blood pressure monitoring instrument that can be used to monitor the blood pressure of a subject who is confined to a hyperbaric chamber. The instrument includes an onboard microprocessor; an inflation pump; inflation gas flow control valves; and a differential pressure transducer, all contained in a portable housing which is positioned outside of the hyperbaric chamber. The pressure cuff is, of course, inside of the chamber. The inflation pump and deflation valves are connected by inflate hoses to the cuff, and the sensor side of the pressure transducer is also connected to the inflate hoses. The exhaust valves are connected to hyperbaric chamber through an exhaust hose. Thus the cuff is inflated with gas from the chamber and is deflated back into the chamber. The exhaust hose is also connected to the reference side of the differential pressure transducer whereby the transducer can accurately measure cuff pressures with reference to the chamber pressure which acts on the exterior of the cuff. The electronics in the instrument are conventional in the art and substantially the same as shown in U.S. Pat. No. 4,796,184, granted Jan. 3, 1989 to D. E. Bahr et. al. The differential between the chamber pressure and cuff pressure is thus registered as "Cuff pressure". The inflation pump preferred for use in the device is a rotary vane pump which pumps gas from the chamber, pressurizes that gas, and pumps it into the cuff. This type of pump solves the problem of pumping an already superatmospheric pressure gas into the cuff to inflate the cuff to even higher pressures. Inflating the cuff with gas from the inside of the chamber overcomes the problem of the high pressure acting on the outside of the cuff.

It is therefore an object of this invention to provide an automatic blood pressure monitor which can be used to monitor the blood pressure of a subject who is confined to a hyperbaric chamber.

It is an additional object of this invention to provide a blood pressure monitor of the character described which inflates the pressure cuff with gas from hyperbaric chamber.

It is a further object of this invention to provide a blood pressure monitor of the character described which exhausts the cuff into the hyperbaric chamber.

It is an additional object of this invention to provide a blood pressure monitor of the character described which uses a differential pressure transducer referenced to the hyperbaric pressure chamber to sense cuff pressure and arterial cuff pressure oscillations.

These and other objects and advantages of the invention will become more readily apparent from the following detailed description thereof when taken in conjunction with the accompanying drawing which is a schematic representation of a preferred embodiment of the invention.

BRIEF DESCRIPTION OF THE DRAWING

FIGURE 1 is a detailed schematic of the blood pressure system of the invention.

DESCRIPTION OF THE PREFERRED EMBODIMENT

The mechanical and electrical components of the device are contained in a casing 2 which is similar to that shown in U.S. Pat. No. 4,796,184, granted Jan. 3, 1989. Inside of the casing 2 is differential pressure transducer 4, a rotary vane pump 6, and a gas flow manifold 8. The positive or sensing side of the pressure transducer 4 is connected to the electronic components 10 of the instrument. An inflating/sensing line or hose 12 extends from the casing 2 to the hyperbaric chamber 14, and an exhaust/reference line or hose 16 extends between the hyperbaric chamber 14 and the casing 2. The exhaust hose 16 opens into the interior of the hyperbaric chamber 14 via reference tube 18, and opens into the negative or reference side of the pressure transducer 4 via line 20. An exhaust line 22 connects the manifold 8 with the exhaust hose 16. A valve 24 controls gas flow through the line 22.

A line 26 connects the inflation/sensing hose 12 with the positive side of the pressure transducer 4, and a line 28 connects the outlet side of the pump 16 with the inflation/sensing hose 12. A valve 30 controls flow of gas through the line 28. A line 32 connects the valve 24 with the inlet side of the pump 16, and a line 34 connects the valve 30 with the inlet side of the manifold 8. The valves 24 and 30 are two way valves which operate to change the direction of gas flow through the lines 22, 28, 32, and 34, as will be described in greater detail hereinafter. The cuff 36 is disposed inside of the hyperbaric chamber 14 and is connected in the inflation/sensing hose 12 by a line 38.

The device operates as follows. When the cuff 36 is to be inflated, the valve 24 is actuated to allow gas flow from the hyperbaric chamber 14 through the hose 6 and lines 22, 32 to the supply side of the pump 16. The valve 30 is actuated to allow gas flow from the pressure side of the pump 6 to the cuff 36 through the line 28, hose 12 and line 38. The pump 6 is actuated to inflate the cuff. The gas used to inflate the cuff 36 is thus pumped from the hyperbaric chamber 14 into the cuff 36. The reference pressure for determining the ΔP in the cuff 36 is the pressure in the hyperbaric chamber 14, which is sensed by the reference side of the pressure transducer 4 through the hose 16 and line 20. The pressure in the cuff 36 is sensed by the opposite side of the transducer 4 through the hose 12 and line 26. When the predetermined ΔP is reached, the pump 6 is deactivated, and the valves 24 and 30 are actuated to begin the deflate the cuff 36. The deflation may be continuous or may be done stepwise, as taught by the prior art. The cuff pressure is sensed by the transducer 4, and arterial oscillations in the cuff pressure, if an oscillatory format is used, are also sensed by the transducer. Observed data are stored in the microprocessor in a conventional manner. During deflation, the valve 30 is actuated to allow gas to flow from the cuff 36 through the hose 12 and lines 28, 34 to the supply side of the manifold 8, and the valve 24 is actuated to allow gas to flow from the manifold 8 through the line 22 and hose 16 back into the hyperbaric chamber 14.

The device of this invention can be used with any automatic blood pressure monitor, as for example, with monitors using auscultatory, oscillometric, ultrasonic, photoplethysmographic or the like techniques. The device could be used with a lower than ambient pressure chamber, should such a chamber prove useful in treating human maladies. The device allows constant blood pressure monitoring of patients in hyperbaric chambers thereby extending the utility of such chambers for the treatment of humans.

Since many changes and variations of the disclosed embodiment of the invention may be made without departing from the invention concept, it is not intended to limit the invention otherwise than as required by the appended claims.

What is claimed is:

1. An assembly for measuring the blood pressure of a subject disposed in a chamber whose internal pressure is different than atmospheric pressure, said assembly comprising:
   (a) a cuff in the chamber for securement to an appendage of the subject;
   (b) means located externally of the chamber for inflating said cuff;
   (c) means located externally of the chamber for sensing and storing cuff pressure valves, said means for sensing and storing including a differential pressure transducer;
   (d) means for connecting a pressure sensing side of said differential pressure transducer with the interior of said cuff; and
   (e) means for connecting a reference side of said differential pressure transducer to a pressure source equalling the pressure in the interior of the chamber.

2. The assembly of claim 1 further including means for connecting said means for inflating to the interior of the chamber whereby said cuff is inflated with gas from the interior of the chamber.

3. The assembly of claim 2 wherein said means for inflating is a rotary vane pump.

4. The assembly of claim 2 further including means for exhausting inflation gas from said cuff, said means for exhausting being connected to the interior of the chamber whereby gas from said cuff is exhausted into the chamber.

5. The assembly of claim 1 further wherein the chamber is a hyperbaric chamber.

6. An assembly for measuring the blood pressure of a subject disposed in a hyperbaric chamber, said assembly comprising:
   (a) a cuff in the hyperbaric chamber for securement to an appendage of the subject;
   (b) a rotary vane pump disposed outside of the chamber, said pump being connected to said cuff and operable to inflate the latter;
   (c) means connecting an inlet side of said pump with the interior of the chamber whereby said pump inflates said cuff with gas from the interior of said chamber; and
   (d) means for sensing and recording cuff pressure values.

7. The assembly of claim 6 further including means for exhausting gas from said cuff, said means for exhausting being connected to the interior of the chamber whereby gas is exhausted from said cuff into the interior of the chamber.

8. The assembly of claim 6 further comprising a differential pressure transducer in said means for sensing and recording; means for connecting a reference side of said differential pressure transducer to the interior of the chamber whereby the transducer is referenced to the pressure inside of the chamber; and means for connecting a sensing side of said differential pressure transducer to the interior of said cuff whereby the transducer is exposed to internal cuff pressure.

9. A method for measuring the blood pressure of a subject disposed in a hyperbaric chamber, said method comprising the steps of:
   (a) attaching a pressure cuff to an appendage of the subject;
   (b) inflating the pressure cuff with gas derived from the interior of the hyperbaric chamber;
   (c) providing a cuff pressure sensor for sensing the internal pressure of the pressure cuff, said cuff pressure sensor including a differential pressure transducer;
   (d) referencing said transducer to the interior pressure in the hyperbaric pressure chamber; and
   (e) sensing internal cuff pressure with said transducer.

10. The method of claim 9 comprising the further step of exhausting gas from said cuff into the interior of the chamber.

11. The method of claim 9 wherein said inflating step is performed with a rotary vane pump.

* * * * *